United States Patent
Hagiya et al.

(10) Patent No.: US 10,174,284 B2
(45) Date of Patent: Jan. 8, 2019

(54) MEDIUM, FOR CULTURING CORNEAL ENDOTHELIAL CELLS, CONTAINING CONDITIONED MEDIUM FROM MESENCHYMAL STEM CELLS

(71) Applicants: JCR PHARMACEUTICALS CO., LTD., Hyogo (JP); THE DOSHISHA, Kyoto (JP); KYOTO PREFECTURAL PUBLIC UNIVERSITY CORPORATION, Kyoto (JP)

(72) Inventors: Michio Hagiya, Hyogo (JP); Kiwamu Imagawa, Hyogo (JP); Yuuki Hosoda, Hyogo (JP); Noriko Koizumi, Kyoto (JP); Naoki Okumura, Kyoto (JP); Makiko Nakahara, Kyoto (JP); Shigeru Kinoshita, Kyoto (JP)

(73) Assignees: JCR PHARMACEUTICALS CO., LTD. (JP); THE DOSHISHA (JP); KYOTO PREFECTURAL PUBLIC UNIVERSITY CORPORATION (JP)

(*) Notice: Subject to any disclaimer, the term of this patent is extended or adjusted under 35 U.S.C. 154(b) by 295 days.

(21) Appl. No.: 14/425,354

(22) PCT Filed: Sep. 5, 2013

(86) PCT No.: PCT/JP2013/073989
§ 371 (c)(1),
(2) Date: Mar. 3, 2015

(87) PCT Pub. No.: WO2014/038639
PCT Pub. Date: Mar. 13, 2014

(65) Prior Publication Data
US 2015/0210981 A1    Jul. 30, 2015

(30) Foreign Application Priority Data
Sep. 7, 2012    (JP) ................................ 2012-196725

(51) Int. Cl.
C12N 5/00       (2006.01)
A61K 35/30      (2015.01)
A61K 35/44      (2015.01)
C12N 5/079      (2010.01)

(52) U.S. Cl.
CPC .......... C12N 5/0621 (2013.01); A61K 35/30 (2013.01); C12N 5/0018 (2013.01); A61K 35/44 (2013.01); C12N 2500/84 (2013.01); C12N 2502/1358 (2013.01)

(58) Field of Classification Search
None
See application file for complete search history.

(56) References Cited

U.S. PATENT DOCUMENTS 4,959,319 A * 9/1990 Skelnik ............... C12N 5/0621
                                                    435/1.3
6,541,256 B1 * 4/2003 Chen ..................... A61K 38/185
                                                    435/325

FOREIGN PATENT DOCUMENTS

| CN | 1749393 A | 3/2006 |
|---|---|---|
| DE | 3827477 | 2/1990 |
| JP | 2004-024852 | 1/2004 |
| JP | 2005-229869 | 9/2005 |
| JP | 2006-187281 | 7/2006 |
| JP | 2006-204527 | 8/2006 |
| JP | 2010-500047 | 1/2010 |
| WO | WO 2009/028631 A1 | 3/2009 |
| WO | WO 2013/100208 A1 | 7/2013 |

OTHER PUBLICATIONS

Chen et al., Paracrine Factors of Mesenchymal Stem Cells Recruit Macrophages and Endothelial Lineage Cells and Enhance Wound Healing, PLOS One, Apr. 2008 | vol. 3 | Issue 4 | e1886.*
Timmers et al., Human mesenchymal stem cell-conditioned medium improves cardiac function following myocardial infarction, Stem Cell Research (2011) 6, 206-214.*
Zhu et al., Proliferative Response of Corneal Endothelial Cells from Young and Older Donors, Investigative Ophthalmology & Visual Science, Jun. 2004, vol. 45, No. 6.*
Numata et al., Cultivation of Corneal Endothelial Cells on a Pericellular Matrix Prepared from Human Decidua-Derived Mesenchymal Cells, PLOS ONE, Feb. 2014, vol. 9, Issue 2.*
International Search Report dated Oct. 8, 2013 in corresponding PCT International Application No. PCT/JP2013/073989.
X. Lu et al., "Enhanced survival in vitro of human corneal endothelial cells using mouse embryonic stem cell conditioned medium," Molecular Vision 16:611-622 (2010).
M.J. Lee et al., "Enhancement of wound healing by secretory factors of endothelial precursor cells derived from human embryonic stem cells," Cytotherapy 13:165-178 (2011).
M.N.M. Walter et al., "Mesenchymal stem cell-conditioned medium accelerates skin wound healing: An in vitro study of fibroblast and keratinocyte scratch assays," Experimental Cell Research 316:1271-1281 (2010).
C-Y. Wang et al., "Mesenchymal Stem Cell-Conditioned Medium Facilitates Angiogenesis and Fracture Healing in Diabetic Rats," Mol. Ther. 19(7):1394 (2011); Abstract #924 of Late Abstracts: Presented at the American Society of Gene & Cell Therapy's 15th Annual Meeting, May 18-21, 2011, Seattle, Washington.
(Continued)

Primary Examiner — Taeyoon Kim
Assistant Examiner — Srikanth Patury
(74) Attorney, Agent, or Firm — Ostrolenk Faber LLP

(57) ABSTRACT

[Problem] To provide, in order to manufacture cells to transplant into patients with corneal endothelial failure, a medium used to culture corneal endothelial cells obtained from human corneal tissue and grow said cells while maintaining the morphology thereof as corneal endothelial cells. [Solution] A medium containing a conditioned medium from mesenchymal stem cells; and a method in which said medium is used to culture corneal endothelial cells.

14 Claims, 5 Drawing Sheets

(56) References Cited

OTHER PUBLICATIONS

G.S.L. Peh et al., "Human Corneal Endothelial Cell Expansion for Corneal Endothelium Transplantation: An Overview," Transplantation 91(8):811-819 (2011).

N.C. Joyce et al., "Human Corneal Endothelial Cell Proliferation—Potential for Use in Regenerative Medicine," Cornea 23 (Suppl. 1):S8-S19 (2004).

Noriko Koizumi, "Development of new therapeutic modalities for corneal endothelial disease using somatic stem cells," Journal of Clinical and Experimental Medicine 241(10):765-770 (2012).

N. Koizumi et al., "Progress in the Development of Corneal Endothelial Tissue Engineering for Future Clinical Application," The Science and Engineering Review of Doshisha University 52(4):31-36 (2012).

M. Nakahara et al., "Corneal Endothelial Expansion Promoted by Human Bone Marrow Mesenchymal Stem Cell-Derived Conditoned Medium," PLoS ONE 8(7):e69009 (2013).

F.W. Price, Jr. et al. "Descemet's Stripping with Endothelial Keratoplasty in 50 Eyes: A Refractive Neutral Corneal Transplant," Journal of Refractive Surgery 21:339-345 (2005).

K. Miyata et al., "Effect of Donor Age on Morphologic Variation of Cultured Human Corneal Endothelial Cells," Cornea 20(1):59-63 (2001).

K. Watanabe et al., "A ROCK inhibitor permits survival of dissociated human embryonic stem cells," Nature Biotechnology 25(6):681-686 (2007).

The Effect of Mesenchymal Stem Cell Conditioned Media on Corneal Stromal Fibroblast Wound Healing Activities in the Br J Ophthalmol (British Journal of Ophthalmology), Aug. 2010; 94(8): 1067-73. doi: 10.1136/bjo.2009.165837. Epub Dec. 3, 2009 by Watson SL, Marcal H, Sarris M, Di Girolamo N, Coroneo MT, Wakefield D.

\* cited by examiner

[Figure 1]
(A)    (B)
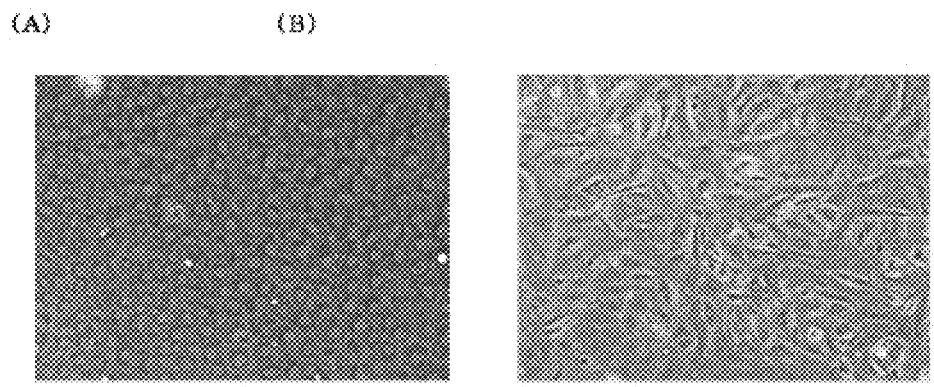
[Figure 2]
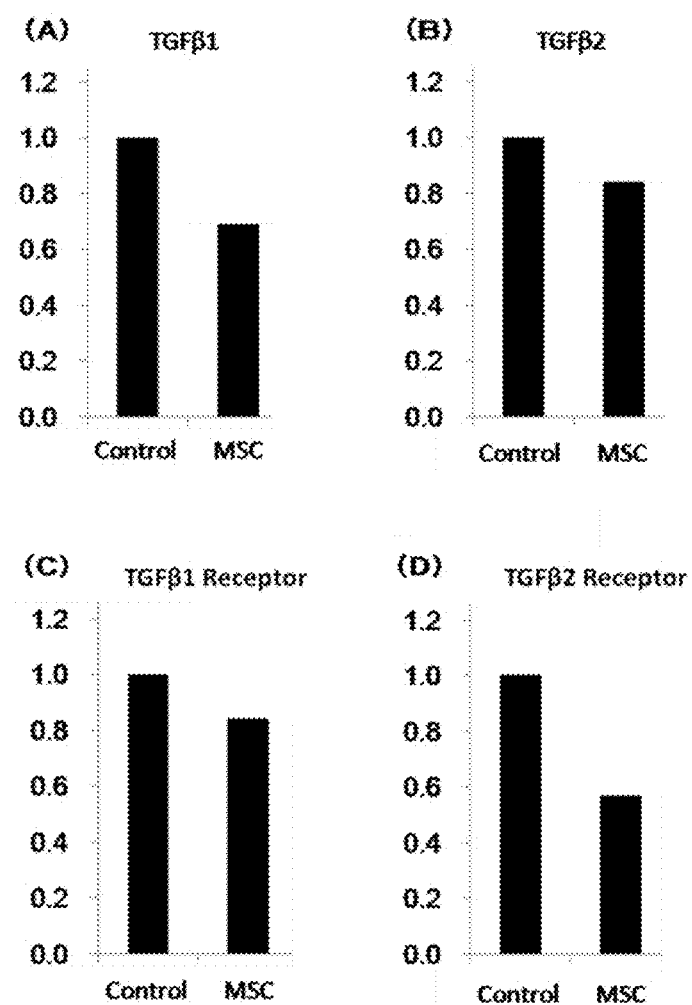

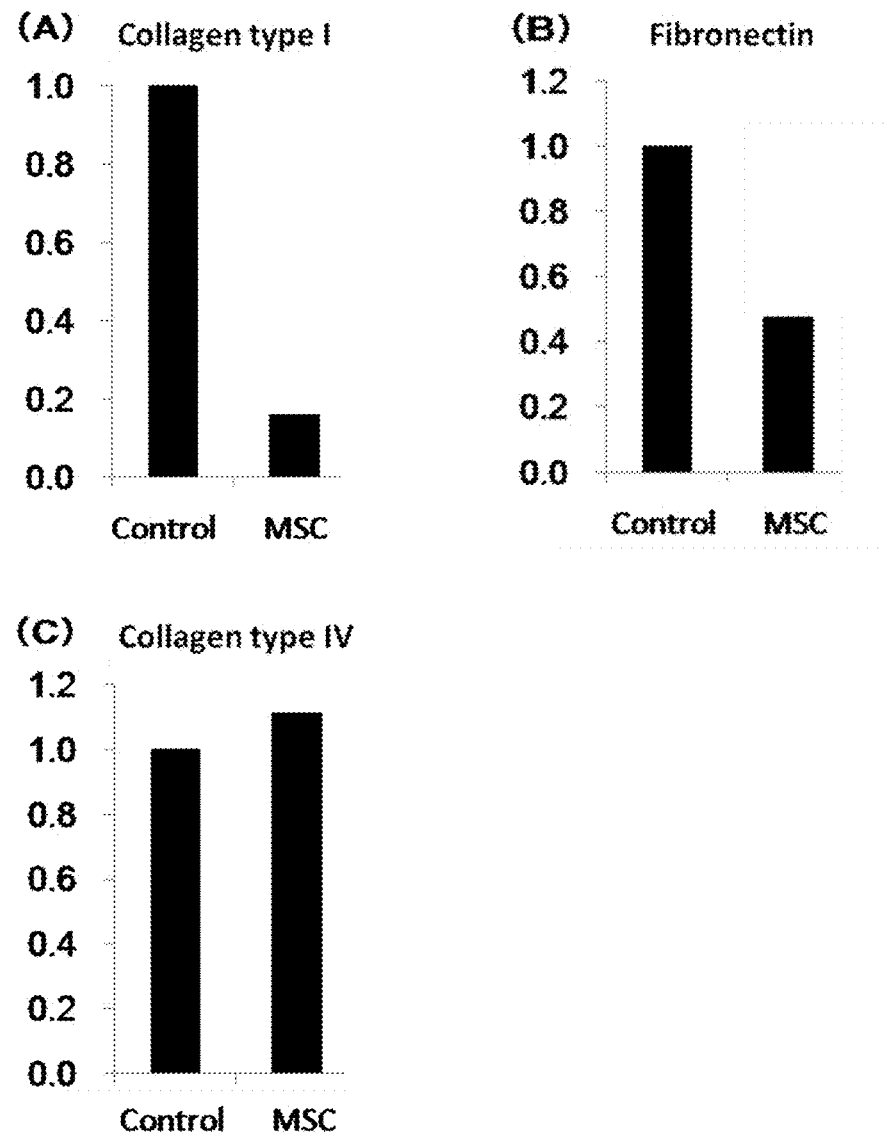
[Figure 3]

[Figure 4]
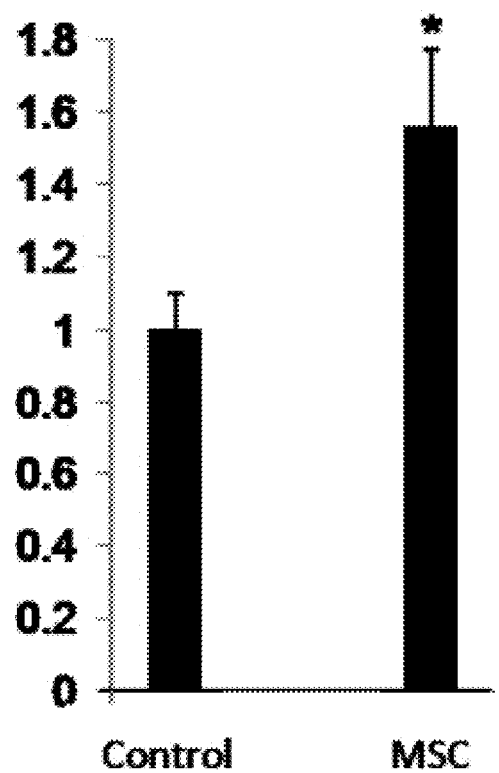

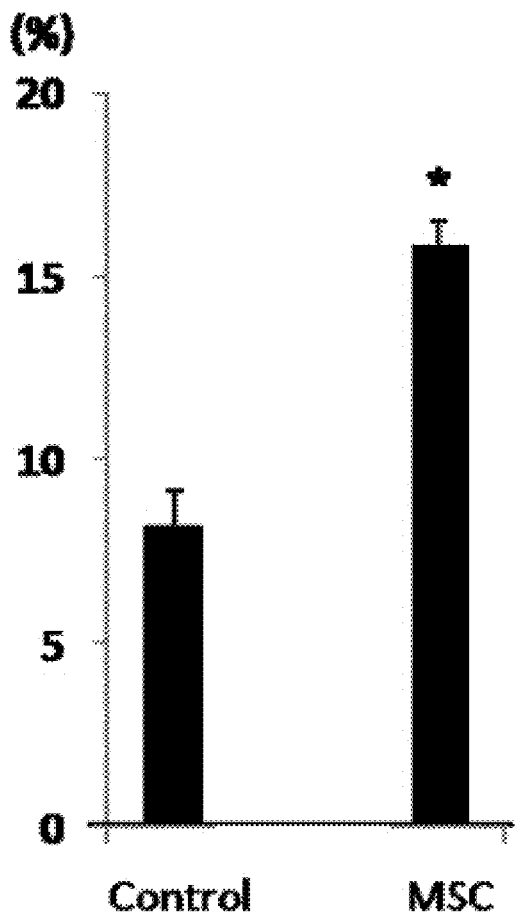
[Figure 5]

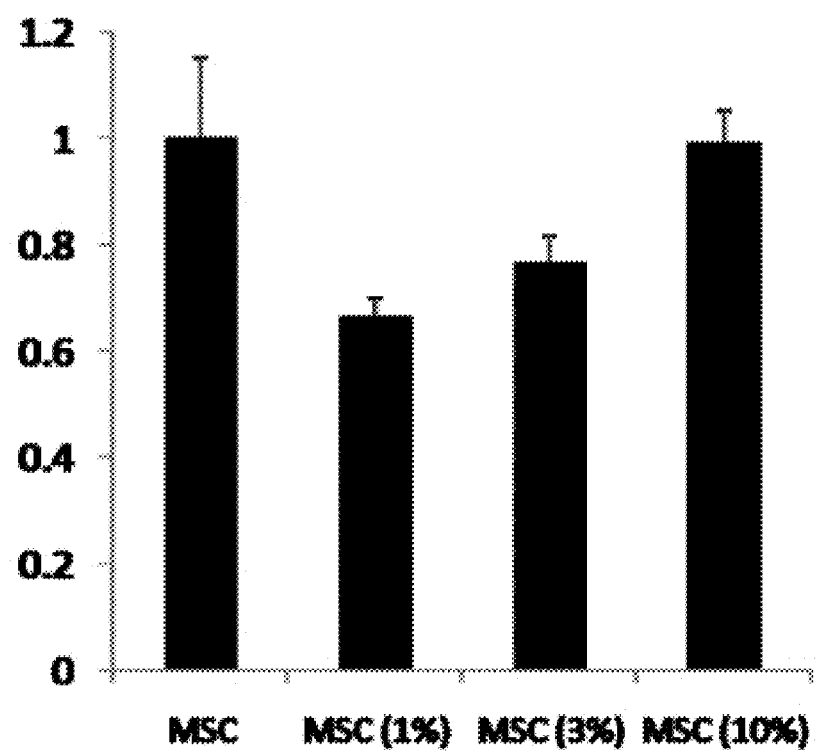
[Figure 6]

MEDIUM, FOR CULTURING CORNEAL ENDOTHELIAL CELLS, CONTAINING CONDITIONED MEDIUM FROM MESENCHYMAL STEM CELLS

CROSS-REFERENCE TO RELATED APPLICATIONS

The present application is a 35 U.S.C. §§ 0 371 national phase conversion of PCT/JP2013/073989, filed Sep. 5, 2013, which claims priority to Japanese Patent Application No. 2012-196725, filed Sep. 7, 2012, the contents of which are incorporated herein by reference. The PCT International Application was published in the Japanese language.

FIELD OF INVENTION

The present invention relates to a method for culturing corneal endothelial cells used for transplantation, and in particular to a medium supplemented with conditioned medium of mesenchymal stem cell for culturing corneal endothelial cells used for transplantation.

BACKGROUND OF THE INVENTION

Cornea is a transparent tissue comprising five cellular layers, i.e. corneal epithelium, Bowman membrane, corneal stromal layer, Descemet's membrane, and corneal endothelium from outside to inside in the order, contains no blood vessel but nerves. Transparency of cornea is maintained by corneal stromal layer and corneal epithelium.

Corneal endothelial dysfunction is one of the main causes of blindness. The loss of function of corneal endothelium for maintaining transparency of cornea results in the impairment of eyesight. Corneal endothelial dysfunction is a disease caused by the degeneration, necrosis or physical loss of corneal endothelium or the like. Bullous keratopathy is a disease caused by severe corneal endothelial dysfunction, in which a pomp function, one of the functions of corneal endothelial cell, to regulate the amount of water in cornea is impaired, and as a result, the water in the cornea in not discharged and the cornea becomes edematous and opacified. In addition, there are cases where corneal epithelium stripped off by edema.

The density of corneal endothelial cells on normal cornea is about 2500 to 3000 cell/mm$^2$, but the density decreases in a condition of corneal endothelial dysfunction. When the cell density becomes about 500 cells/mm$^2$ or less, the pumping function and the barrier function of corneal endothelial cells decline resulting in edema.

Corneal endothelial cells cannot regenerate, once injured. As the therapy for the corneal endothelial dysfunction, penetrating keratoplasty has been performed to recover the function of corneal endothelium and the transparency of cornea as well, where healthy cornea which possesses the three-layer structure comprising epithelium, stroma, and endothelium is transplanted. However penetrating keratoplasty has a problem such as vulnerability of eyeball caused by dissection of all the layer of cornea. Therefore, DSAEK (Descemet's Stripping Automated Endothelial Keratoplasty) in which only corneal endothelium has been transplanted, and DMEK (Descemet's Membrane Endothelial Keratoplasty) in which corneal endothelium has been transplanted with Descemet's membrane have been recently prevailing (NPL 1). The examples of diseases caused by the dysfunction of corneal endothelium and requiring corneal transplantation, include corneal edema, corneal leukoma, conical cornea, and the like, in addition to bullous keratopathy. In Japan, the number of patients waiting for corneal transplantation is about 5500, but the annual number of corneal transplantation is about 2700. The current situation is that sufficient actions to the patients cannot be taken due to donor shortage.

As the method to solve donor shortage as above, studies have been made to culture corneal endothelial cells and transplant them to the patients with corneal endothelial dysfunction to recover the function of corneal endothelium. For example, a method for production of a corneal endothelium-like sheet for transplantation by culturing corneal endothelial cells on amnion has been reported (PTL 1 and 2). In these reports, DMEM medium containing 10% FCS, 2 ng/mL of b-FGF, and antibiotics (PTL 1), or DMEM medium containing 10% FCS (PTL 2) was used as the medium for corneal endothelial cell culture. Furthermore a method for production of a corneal endothelium-like sheet for transplantation by culturing corneal endothelial cells on a collagen sheet coated with fibronectin has been reported (PTL 3), and a method for production of a corneal endothelium-like sheet for transplantation by culturing corneal endothelial cells on a cellulose substrate has been reported (PTL 4). In these reports, low glucose DMEM medium supplemented with 15% FCS, 2 ng/mL of b-FGF, and antibiotics was used as a medium for corneal endothelial cell culture. And it has been reported that hyaluronic acid, EGF, and the like can be added to the medium. Several media have been reported as the media for corneal endothelial cell culture (NPL 2).

There is a problem with the culture of corneal endothelial cells, in which corneal endothelial cells morphologically change to fibroblast-like cell during culture period (PTL 4 and NPT 3).

A method to produce a corneal endothelial cell layer with high cell density for transplantation has been reported, in which the corneal endothelial cells are cultured in the presence of a Rho kinase inhibitor to prevent the morphological change of the cells and to promote the cell attachment (PTL 5). In this report, a low glucose DMEM medium supplemented with 15% FCS, 2 ng/mL of b-FGF, and antibiotics has been used as a basal medium for corneal endothelial cell culture (NPT 4). It has been known that Rho kinase is activated when cell death of human ES cells occurs during the culture, and ROCK inhibitors, such as (+)trans-4-(1-aminoethyl)-1-(4-pyridylcarbamoyl) cyclohexane and 1-(5-Isoquinolinesulfonyl)homopiperazine, prevent this cell death (NPT 5).

Furthermore, a method for culturing corneal endothelial cells has been known, in which Opti-MEM-1 (mfd. by Gibco) supplemented with 20 ng/mL of NGF, 5 ng/mL of EGF, 20 µg/mL of ascorbic acid, 200 µg/mL of CaCl$_2$, 100 µg/mL of pituitary extract, 0.08% (w/v) of chondroitin sulfate and antibiotics is used (NPT 6). However, transplant therapy has not yet been in practical use for improving the function of corneal endothelium of the patient with corneal endothelial dysfunction using the cells obtained by culturing corneal endothelial cells.

CITATION LIST

Patent Literature

PTL 1: JP2004-024852
PTL 2: JP2006-187281
PTL 3: JP2005-229869

PTL 4: JP2006-204527
PTL 5: WO2009/028631

Non Patent Literature

NPL 1: Price F W. Jr. et al., J Refract Surg. 21, 339-45 (2005)
NPL 2: Peh G S L. et al., Transplantation 91, 811-9 (2011)
NPL 3: Koizumi N. et. al., The science Engineering Review of Doshisha Univ. 52, 31-36 (2012)
NPL 4: Miyata K. et al., Cornea 20, 59-63 (2001)
NPL 5: Watanabe K. et al., Nat Biotechnol. 25, 681 (2007)
NPL 6: Joyce N C. Et al., Cornea 23, S8-19 (2004)

SUMMARY OF INVENTION

Technical Problem

Based on the above background, the objective of the present invention is to provide a method for culturing the cells which are applicable to the transplant therapy to improve the function of corneal endothelium of the patient with corneal endothelial dysfunction.

Solution to Problem

In a study for the above-mentioned object, the present inventors found that the cells morphologically similar to corneal endothelial cell and free from fibroblast-like cell could be obtained by culturing corneal endothelial cells with a conditioned medium of mesenchymal stem cell (MSC conditioned medium) or a medium containing MSC conditioned medium, and completed the present invention. Thus the present invention provides what follows:

(1) A medium for corneal endothelial cell culture consisting of a conditioned medium of mesenchymal stem cell or containing the conditioned medium.
(2) The medium for corneal endothelial cell culture according to (1) above, containing the conditioned medium in a proportion of 0.5 to 50% (v/v).
(3) The medium for corneal endothelial cell culture according to (1) above, containing the conditioned medium in a proportion of 1 to 10% (v/v).
(4) The medium according to any one of (1) to (3) above, wherein the conditioned medium is obtained by culturing a mesenchymal stem cell in a medium containing chondroitin sulfate at a concentration of 0.04 to 0.12% (w/v).
(5) The medium according to (4) above, wherein the concentration of chondroitin sulfate is 0.08% (w/v).
(6) A medium for corneal endothelial cell culture containing a concentrated solution obtained by filtration concentration of a conditioned medium of mesenchymal stem cell.
(7) The medium for corneal endothelial cell culture according to (6) above, wherein the concentration rate in the filtration concentration is 2 to 30 times.
(8) The medium for corneal endothelial cell culture according to (6) above, wherein the concentration rate in the filtration concentration is 15 to 20 times.
(9) The medium for corneal endothelial cell culture according to any one of (6) to (8) above, containing the concentrated solution at a proportion of 0.5 to 50% (v/v).
(10) The medium for corneal endothelial cell culture according to any one of (6) to (8) above, containing the concentrated solution at a proportion of 1 to 10% (v/v).
(11) The medium for corneal endothelial cell culture according to any one of (6) to (10) above, wherein the conditioned medium is obtained by culturing the mesenchymal stem cell in a medium containing chondroitin sulfate at a concentration of 0.04 to 0.12% (w/v).
(12) The medium according to (11) above, wherein the concentration of chondroitin sulfate is 0.08% (w/v).
(13) The medium according to any one of (1) to (12) above, wherein the mesenchymal stem cell is human mesenchymal stem cell.
(14) The medium according to any one of (1) to (12) above, wherein the mesenchymal stem cell is a mesenchymal stem cell derived from human bone marrow.
(15) A method for culturing corneal endothelial cells, which comprises a step for separating the corneal endothelial cells from a corneal tissue and a step for propagating the separated corneal endothelial cells by a culture using the medium according to any one of (1) to (14) above.
(16) The cells obtained by the method for culture according to (15) above.
(17) The cells according to (16) above, containing cells expressing both of Na+/K+-ATPase and ZO-1 in a proportion of 80% or more.
(18) The cells according to (16) or (17) above, wherein the mixing ratio of fibroblast-like cells is less than 0.2%.
(19) The cells according to any one of (16) to (18) above, containing Ki-67 positive cells in a proportion of 10% or more.
(20) A therapeutic agent for corneal endothelial dysfunction containing the cells according to any one of (16) to (19) above.
(21) The therapeutic agent according to (20) above, wherein the corneal endothelial dysfunction is bullous keratopathy.

Advantageous Effects of Invention

The present invention enables stable supply of corneal endothelial cells having a constant quality and transplantable to a patient with corneal endothelial dysfunction, thus solving donor shortage for corneal transplantation.

BRIEF DESCRIPTION OF DRAWINGS

FIG. 1 is the magnified drawing showing the appearance of cultured human corneal endothelial cells. FIGS. 1(A) and (B) respectively indicate appearance of the cells cultured in MSC conditioned medium, and the cells cultured in the basal medium (control culture).

FIG. 2 shows the expression levels of TGF related genes in the cells cultured using MSC conditioned medium (MSC), and in the cells cultured using the basal medium (control culture), measured by real-time PCR method. FIGS. 2 (A), (B), (C), and (D) respectively represent the expression level of TGFβ1, TGFβ2, TGFβ1 receptor, and TGFβ2 receptor. The expression levels are indicated as the relative amount against the expression level of control-cultured cells being 1.0 (vertical axis).

FIG. 3 shows the expression level of fibroblast-related genes in the cells cultured using MSC conditioned medium (MSC), and in the cells cultured using the basal medium (control culture), measured by real-time PCR method. FIGS. 3 (A), (B), and (C) respectively represent the expression level of collagen type I, fibronectin, collagen type IV. The expression levels are indicated as the relative amount against the expression level of control-cultured cells being 1.0 (vertical axis).

FIG. 4 shows the results of measurement of cell growth of the cells cultured using MSC conditioned medium (MSC), and of the cells cultured using the basal medium (control culture) based on BrdU uptake rate. BrdU uptake rate is indicated as the relative value against the BrdU uptake rate of control-cultured cells being 1.0 (vertical axis). Asterisk indicates the statistically-significant difference (p<0.05) according to t-test (n=3).

FIG. 5 shows the ratio of Ki-67 protein-positive cell (%) in the cells cultured using MSC conditioned medium (MSC), and in the cells cultured using the basal medium (control culture). Asterisk indicates the statistically-significant difference (p<0.05) according to t-test (n=3).

FIG. 6 shows the result of addition test of concentrated solution of MSC conditioned medium. BrdU uptake rate is indicated as the relative value against the BrdU uptake rate of the cell cultured using MSC conditioned medium being 1.0 (vertical axis).

DETAILED DESCRIPTION OF THE INVENTION

In the present invention, mesenchymal stem cell (MSC) means the cell having a potential to proliferate in undifferentiated state and differentiate at least two types of cell, including the stem cell derived from mesenchyme and its progenitor cell. The cells inducible from mesenchymal stem cell by differentiation, for example, are osteoblast, chondroblast, and lipoblast.

MSC used in the present invention is preferably human mesenchymal stem cell (hMSC). It has been well known that MSC can be obtained from several tissues including bone marrow, adipose tissue, dental pulp, umbilical blood, placenta, amnion, and so on. All of these MSCs can be used as the MSC in the present invention regardless of their source, but bone marrow-derived MSC is preferable. The hMSCs can be prepared in several ways. For example, in the case of bone marrow-derived hMSCs, they can be prepared by the method described in a patent literature (JP H07-500001) and so on.

The human mesenchymal stem cells used in the present invention can be further characterized by the pattern of surface antigen expression, and when analyzed flow cytometrically using specific antibodies, the hMSC is preferably positive for CD29, CD44, and CD105, and negative for CD34 and CD45; more preferably positive for CD29, CD44, CD73, CD90, and CD105, and negative for CD34 and CD45; still more preferably positive for CD13, CD29, CD44, CD73, CD90, CD105, and CD166, and negative for CD34 and CD45; and further more preferably positive for CD13, CD29, CD44, CD49a, CD49e, CD73, CD90, CD105, and CD166, and negative for CD34 and CD45.

In the present invention, the term "conditioned medium of mesenchymal stem cell (MSC conditioned medium)" means the medium obtained by culturing the mesenchymal stem cells in a medium and then removing the cells.

In the present invention, there is no particular limitation as to the type of culture medium used for the culture of MSC to prepare the MSC conditioned medium, and for example, BGJb medium (Fitton-Jackson Modification) containing fetal calf serum (FCS); F-12 nutrient mixture (Ham) supplemented with fetal calf serum (FCS); DMEM medium supplemented d with fetal calf serum (FCS); Dulbecco/Ham's F12 1:1 mixed medium supplemented with fetal calf serum (FCS); Dulbecco/Ham's F12 1:1 mixed medium supplemented with 4 mM of alanylglutamine; Opti-MEM™ I Reduced-Serum Medium Liquid (mfd. by Gibco) supplemented with fetal calf serum (FCS); Opti-MEM™ I Reduced-Serum Medium Liquid (mfd. by Gibco) supplemented with fetal calf serum (FCS), 200 µg/mL of $CaCl_2 \cdot 2H_2O$, and 0.08% (w/v) chondroitin sulfate; and the like may be used. The concentration of fetal calf serum contained in the medium as above is preferably 5 to 20% (v/v), more preferably 6 to 12% (v/v), still more preferably 7.5 to 10.5%(v/v), and when Opti-MEM™ I Reduced-Serum Medium Liquid to be used, the concentration is especially about 8% (v/v), and when other basal medium to be used, the concentration is about 1%. Here, the Opti-MEM™ I Reduced-Serum Medium Liquid (mfd. by Gibco) is a Basal Eagle Medium supplemented with HEPES, sodium bicarbonate, hypoxanthine, thymidine, sodium pyruvate, L-glutamine, insulin, transferrin, and so on to.

The culture medium for MSC before adding fetal calf serum contains amino acids, vitamins, inorganic salts, and other ingredients. The type and concentration of amino acids contained in the culture medium for MSC are selected from those shown in table 1 as needed.

TABLE 1

The type and concentration of amino acids contained in the culture medium for MSC (before adding fetal calf serum)

|  | mM |
| --- | --- |
| Glycine | 0~12.8 |
| L-Alanine | 0~3.4 |
| L-Alanyl-L-Glutamine | 0~1.2 |
| L-Glutamine | 0~5 |
| L-Arginine | 0.48~1.2 |
| L-Asparagine | 0~1.2 |
| L-Aspartic acid | 0~1.4 |
| L-Cysteine | 0.08~0.7 |
| L-Glutamic Acid | 0~0.12 |
| L-Histidine | 0.12~1.2 |
| L-Isoleucine | 0.028~1.0 |
| L-Leucine | 0.08~1.0 |
| L-Lysine | 0.16~2.0 |
| L-Methionine | 0.025~0.4 |
| L-Phenylalanine | 0.025~0.5 |
| L-Proline | 0~4.2 |
| L-Serine | 0~0.3 |
| L-Threonine | 0.08~0.96 |
| L-Tryptophan | 0.008~0.095 |
| L-Tyrosine | 0.024~0.48 |
| L-Valine | 0.08~1.0 |
| L-Cystine | 0.08~0.12 |

The type and concentration of vitamins contained in the culture medium for MSC are selected from those shown in table 2 as needed.

TABLE 2

The type and concentration of vitamins contained in the culture medium for MSC (before adding fetal calf serum)

|  | mM |
| --- | --- |
| Biotin | 0~0.001 |
| Choline chloride | 0.0056~0.12 |
| D-Calcium pantothenate | 0.00032~0.01 |
| Folic Acid | 0.00036~0.011 |
| Niacinamide | 0.00023~0.2 |
| Pyridoxine | 0~0.024 |
| Pyridoxal phosphate | 0~0.00098 |
| Pyridoxal hydrochloride | 0~0.006 |
| Riboflavin | 0~0.0007 |
| Thiamine hydrochloride | 0.0011~0.015 |
| Vitamin B12 | 0~0.015 |
| i-Inositol | 0.0014~0.12 |
| Ascorbic Acid | 0~0.35 |
| DL-alpha Tocopherol phosphate | 0~0.0018 |
| Para-Aminobenzoic Acid | 0~0.018 |

The type and concentration of inorganic salts contained in the culture medium for MSC are selected from those shown in table 3 as needed.

TABLE 3

The type and concentration of inorganic salts contained in the culture medium for MSC (before adding fetal calf serum)

|  | mM |
|---|---|
| $CaCl_2 \cdot 2H_2O$ | 0~2.2 |
| $CuSO_4 \cdot 5H_2O$ | 0~0.000012 |
| $FeSO_4 \cdot 7H_2O$ | 0~0.0018 |
| $Fe(NO_3)_3 \cdot 9H_2O$ | 0~0.00015 |
| $MgCl_2 \cdot 6H_2O$ | 0~0.85 |
| $MgSO_4$ | 0~0.98 |
| KCl | 2.4~6.4 |
| $KH_2PO_4$ | 0~1.45 |
| $NaHCO_3$ | 1.1~54 |
| NaCl | 70~140 |
| $Na_2HPO_4$ | 0~1.2 |
| $NaH_2PO_4$ | 0~1.2 |
| $ZnSO_4 \cdot 7H_2O$ | 0~0.0036 |

The type and concentration of other ingredients contained in the culture medium for MSC are selected from those shown in table 4 as needed.

TABLE 4

The type and concentration of other ingredients contained in the culture medium for MSC (before adding fetal calf serum)

|  | mM |
|---|---|
| D-Glucose | 4.5~67 |
| Hypoxanthine | 0~0.036 |
| Linoleic Acid | 0~0.00036 |
| Lipoic Acid | 0~0.0012 |
| Phenol Red | 0~0.0035 |
| Putrescine·2HCl | 0~0.0012 |
| Sodium Pyruvate | 0~1.2 |
| Thymidine | 0~0.0035 |
| Calcium lactate | 0~3.1 |
| Sodium Acetate | 0~0.72 |
| HEPES | 0~18 |

Table 5 shows the composition of the mediums preferably used in the present invention as the culture medium for MSC before addition of fetal calf serum. In table 5, medium A is BGJb Medium (Fitton-Jackson Modification), medium B is F-12 nutrient mixture (Ham), medium C is DMEM medium, medium D is Dulbecco/Ham's F12, 1:1 mixed medium, medium E is EMEM medium.

To the medium, one or more of other ingredients selected from growth factors such as epidermal growth factor (EGF), basic fibroblast growth factor (bFGF), nerve growth factor (NGF), insulin, transferrin, insulin like growth factor (IGF), ascorbic acid, chondroitin sulfate, antibiotics such as gentamicin, and pH indicators such as phenol red may be added as needed. In the case EGF is added to the medium, its concentration is preferably 1 to 50 ng/mL, more preferably 5 to 40 ng/mL, and still more preferably about 20 ng/mL. In the case bFGF is added to the medium, its concentration is preferably 1 to 20 ng/mL, more preferably 3 to 7 ng/mL, and still more preferably about 5 ng/mL. In the case NGF is added to the medium, its concentration is preferably 1 to 25 ng/mL, more preferably 3 to 7 ng/mL, and still more preferably about 5 ng/mL. In the case insulin is added to the medium, its concentration is preferably 1 to 200 µg/mL. In the case transferrin is added to the medium, its concentration is preferably 1 to 200 µg/mL. In the case ascorbic acid (or the salt thereof) is added to the medium, its concentration is preferably 5 to 40 µg/mL, more preferably 10 to 30 µg/mL, and still more preferably about 20 µg/mL. In the case chondroitin sulfate (or the salt thereof) is added to the medium, its concentration is preferably 0.04 to 0.12%(w/v), more preferably 0.06 to 0.10%(w/v), and still more preferably about 0.08%(w/v).

When the use of FCS, one of biological materials, is not desirable, serum free medium may be used as a MSC culture medium.

TABLE 5

The composition of the culture mediums for MSC before adding fetal calf serum
(All the concentrations are shown in mM)

|  | Medium A | Medium B | Medium C | Medium D | Medium E |
|---|---|---|---|---|---|
| Glycine | 10.67 | 0.1 | 0.4 | 0.25 | — |
| L-Alanine | 2.81 | 0.1 | — | 0.05 | — |
| L-AlanyL-L-Glutamine | — | 1 | — | — | — |
| L-Glutamine | 1.37 | — | 4 | 2.5 | 2 |
| L-Arginine hydrochloride | 1.01 | 1 | 0.398 | 0.699 | 0.597 |
| L-Asparagine (freebase) | — | 0.0985 | — | 0.05 | — |
| L-Aspartic acid | 1.13 | 0.1 | — | 0.05 | — |
| L-Cysteine hydrochloride | 0.574 | 0.205 | 0.201 | 0.0998 | 0.099 |
| L-Glutamic Acid | — | 0.1 | — | 0.05 | — |
| L-Histidine hydrochloride | 0.968 | 0.1 | 0.2 | 0.15 | 0.2 |
| L-Isoleucine | 0.229 | 0.0305 | 0.802 | 0.416 | 0.397 |
| L-Leucine | 0.382 | 0.1 | 0.802 | 0.451 | 0.397 |
| L-Lysine hydrochloride | 1.64 | 0.199 | 0.798 | 0.499 | 0.399 |
| L-Methionine | 0.336 | 0.0302 | 0.201 | 0.116 | 0.101 |
| L-Phenylalanine | 0.303 | 0.0303 | 0.4 | 0.215 | 0.194 |
| L-Proline | 3.48 | 0.3 | — | 0.15 | — |
| L-Serine | 1.9 | 0.1 | 0.4 | 0.25 | — |
| L-Threonine | 0.63 | 0.1 | 0.798 | 0.449 | 0.403 |
| L-Tryptophan | 0.196 | 0.01 | 0.0784 | 0.0442 | 0.049 |
| L-Tyrosine disodium salt dihydrate | 0.258 | 0.0298 | 0.398 | 0.214 | 0.199 |
| L-Valine | 0.556 | 0.1 | 0.803 | 0.452 | 0.393 |
| L-Cystine | — | — | — | 0.1 | — |
| Biotin | 0.00082 | 0.0000299 | — | 0.0000143 | — |
| Choline chloride | 0.357 | 0.1 | 0.0286 | 0.0641 | 0.00714 |
| D-Calcium pantothenate | 0.000419 | 0.00105 | 0.00839 | 0.0047 | 0.0021 |

TABLE 5-continued

The composition of the culture mediums for MSC before adding fetal calf serum
(All the concentrations are shown in mM)

| | Medium A | Medium B | Medium C | Medium D | Medium E |
|---|---|---|---|---|---|
| Folic Acid | 0.000454 | 0.00295 | 0.00907 | 0.00601 | 0.00227 |
| Niacinamide | 0.164 | 0.000295 | 0.0328 | 0.0166 | 0.0082 |
| Pyridoxine hydrochloride | — | 0.000291 | 0.0196 | 0.00971 | 0.0049 |
| Pyridoxal phosphate | 0.00081 | — | — | — | — |
| Pyridoxal hydrochloride | — | — | — | — | — |
| Riboflavin | 0.000532 | 0.0000984 | — | 0.000582 | 0.000266 |
| Thiamine hydrochloride | 0.0119 | 0.00089 | 0.00106 | 0.00644 | 0.00297 |
| Vitamin B12 | 0.0000295 | 0.00103 | 0.0119 | 0.000502 | — |
| i-Inositol | 0.00111 | 0.1 | 0.04 | 0.07 | 0.0111 |
| Ascorbic Acid | 0.284 | — | — | — | — |
| DL-alpha Tocopherol phosphate | 0.00142 | — | — | — | — |
| Para-Aminobenzoic Acid | 0.0146 | — | — | — | — |
| $CaCl_2 \cdot 2H_2O$ | — | 0.299 | 1.8 | 1.05 | 1.8 |
| $CuSO_4 \cdot 5H_2O$ | — | 0.00001 | — | 0.0000052 | — |
| $FeSO_4 \cdot 7H_2O$ | — | 0.003 | 0.000248 | 0.0015 | — |
| $Fe(NO_3)_3 \cdot 9H_2O$ | — | — | — | 0.000124 | — |
| $MgCl_2 \cdot 6H_2O$ | — | 0.601 | — | 0.301 | 0.814 |
| $MgSO_4$ | 0.817 | — | 0.814 | 0.407 | — |
| KCl | 5.33 | 2.98 | 5.33 | 4.16 | 5.33 |
| $KH_2PO_4$ | 1.18 | — | — | — | — |
| $NaHCO_3$ | 41.67 | 14 | 44.05 | 14.29 | 26.19 |
| NaCl | 91.38 | 131.02 | 110.34 | 120.61 | 117.24 |
| $Na_2HPO_4$ | — | 1 | — | 0.5 | — |
| $NaH_2PO_4$ | 0.652 | — | 0.906 | 0.453 | 1.01 |
| $ZnSO_4 \cdot 7H_2O$ | — | — | — | — | — |
| D-Glucose | 55.56 | — | 25 | 17.51 | 5.56 |
| Hypoxanthine | — | 0.0294 | — | 0.015 | — |
| Linoleic Acid | — | 0.0003 | — | 0.00015 | — |
| Lipoic Acid | — | 0.000971 | — | 0.00051 | — |
| Phenol Red | — | 0.00319 | — | — | — |
| Putrescine·2HCl | — | 0.001 | — | 0.000503 | — |
| Sodium Pyruvate | — | 1 | 1 | 0.5 | — |
| Thymidine | — | 0.00289 | — | 0.00151 | — |
| Calcium lactate | 2.55 | — | — | — | — |
| Sodium Acetate | 0.61 | — | — | — | — |
| HEPES | — | — | — | 15.02 | — |

In the present invention, the culture of MSC for preparing MSC conditioned medium is started by seeding the MSC into the cell culture flask preferably at the density of $1 \times 10^3$ to $2 \times 10^4$ cells/cm$^2$, more preferably at the density of $2 \times 10^3$ to $1 \times 10^4$ cells/cm$^2$, still more preferably at the density of 3 to $5 \times 10^3$ cells/cm$^2$. And in doing this, the volume of the culture medium for MSC added per 1 cm$^2$ of culture area is preferably 0.15 to 0.5 mL, more preferably 0.2 to 0.3 mL. And the cell culture flask used in doing this is preferably a flask whose bottom is coated with collagen, fibronectin, and the like or a flask whose bottom is modified by negatively charged functional group, such as CULTURE WARE FOR PRIMALIA (mfd. by BD). After starting the culture, the MSCs are cultured until the bottom of cell culture flask is occupied by the cells preferably to 30 to 80%, and more preferably to 50 to 70%. And then, the medium was collected (first collection), and the medium is exchanged to the new medium and the cells were further cultured. At this time, the volume of the culture medium added per 1 cm$^2$ of culture area is preferably 0.15 to 0.5 mL, and more preferably 0.2 to 0.3 mL. After exchanging the medium, the cells are cultured preferable for 8 to 24 hours, and more preferably for 12 to 18 hours, and then the medium was collected (second collection) Collection and exchange of the medium is further repeated preferably 3 to 7 times, and more preferably 3 to 5 times in the same manner (third and further collections).

All the media collected at the first collection, at the second collection, and at third and further collections can be used as the MSC conditioned medium, and the mixture thereof may also be used as the MSC conditioned medium, but the media collected at the second and further collections are particularly preferably used. And the collection of MSC conditioned medium is performed preferably by centrifuging the medium and collecting the supernatant. The collected MSC conditioned medium may be sterilized, as needed, by a membrane filtration or the like. And as the MSC conditioned medium can be frozen, the MSC conditioned medium can be stored over a long time or delivered in a frozen state. The MSC conditioned can also be stored at 4° C. for 10 to 14 days.

In the present invention, the MSC conditioned medium may be used as the medium for human corneal endothelial cell culture without any modifications, but to the medium, one or more of other ingredients selected from growth factors such as epidermal growth factor (EGF), basic fibroblast growth factor (bFGF), nerve growth factor (NGF), insulin, transferrin, insulin like growth factor (IGF), ascorbic acid, chondroitin sulfate, antibiotics, and so on may be added as needed. In the case EGF is added to the medium, its concentration is preferably 1 to 50 ng/mL, more preferably 5 to 40 ng/mL, and still more preferably about 20 ng/mL. In the case bFGF is added to the medium, its concentration is preferably 1 to 20 ng/mL, more preferably 3 to 7 ng/mL, and still more preferably about 5 ng/mL. In the case NGF is added to the medium, its concentration is preferably 1 to 25 ng/mL, more preferably 3 to 7 ng/mL, and still more preferably about 5 ng/mL. In the case insulin is added to the medium, its concentration is preferably 1 to 200 µg/mL. In the case transferrin is added to the medium, its concentration is preferably 1 to 200 µg/mL. In the case ascorbic acid (or the salt thereof) is added to the medium, its concentration is preferably 5 to 40 µg/mL, more preferably 10 to 30 µg/mL, and still more preferably about 20 µg/mL. In the case chondroitin sulfate (or the salt thereof) is added to the medium, its concentration is preferably 0.04 to 0.12% (w/v), more preferably 0.06 to 0.10% (w/v), and still more preferably about 0.08% (w/v).

The MSC conditioned medium may be used as the medium for human corneal endothelial cell culture without any modification, but another medium supplemented with the MSC conditioned medium may be used as the medium for human corneal endothelial cell culture. In doing this, the volume of the MSC conditioned medium is preferably 10 to 98%(v/v), more preferably 50 to 98%(v/v), and still more preferably 80 to 98%(v/v), with respect to the volume of the another medium.

And it may be possible to use another medium supplemented with concentrated solution of conditioned medium of human mesenchymal stem cell obtained by concentrating the MSC conditioned medium (concentrated solution of MSC conditioned medium) as a medium for human corneal endothelial cell culture. The concentrated solution of conditioned medium may be prepared by concentrating the MSC conditioned medium by a method such as filtration concentration using an ultrafiltration membrane, vacuum concentration, or freeze drying. The ultrafiltration membrane used in filtration concentration is preferably the membrane whose concentration recovery rate of cytochrome c is 90% or more, such as 10 kDa cut-off membrane (mfd. by Millipore), and more preferably, the membrane whose concentration recovery rate of cytochrome c is 95% or more, such as 3 kDa cut-off membrane (mfd. by Millipore). And the concentration rate (liquid volume before concentration/liquid volume after concentration) is preferably 2 to 30 times, more preferably 10 to 35 times, and still more preferably 15 to 20 times.

In doing this, the ratio of the amount of the concentrated solution of MSC conditioned medium added to another medium is preferably 1 to 20% (v/v), more preferably 2 to 15% (v/v), and still more preferably 3 to 10%(v/v) with respect to the amount of the another medium.

Another medium to which the MSC conditioned medium or the concentrated solution of MSC conditioned medium is to be added is preferably a medium for human corneal endothelial cell culture disclosed in prior arts (Peh G S L. et al., Transplantation 91, 811-9 (2011), and so on), such as Opti-MEM™ I Reduced-Serum Medium Liquid (mfd. by Gibco) supplemented with 8% (v/v) FCS, 200 µg/mL $CaCl_2 \cdot 2H_2O$, 0.08% (w/v) chondroitin sulfate, 20 µg/mL ascorbic acid, and 5 ng/mL EGF, but not limited to this. The media having the compositions shown in Table 5 as above or the media wherein the compositions are adjusted as needed may be also used. And the medium supplemented with one or more of other ingredients selected from growth factors such as epidermal growth factor (EGF), basic fibroblast growth factor (bFGF), nerve growth factor (NGF), insulin, transferrin, insulin like growth factor (IGF), ascorbic acid, chondroitin sulfate, antibiotics, and so on, as needed, may be used. In the case EGF is added to the medium, its concentration is preferably 1 to 50 ng/mL, more preferably 5 to 40 ng/mL, and still more preferably about 20 ng/mL. In the case bFGF is added to the medium, its concentration is preferably 1 to 20 ng/mL, more preferably 3 to 7 ng/mL, and still more preferably about 5 ng/mL. In the case NGF is added to the medium, its concentration is preferably 1 to 25 ng/mL, more preferably 3 to 7 ng/mL, and still more preferably about 5 ng/mL. In the case insulin is added to the medium, its concentration is preferably 1 to 200 µg/mL. In the case transferrin is added to the medium, its concentration is preferably 1 to 200 µg/mL. In the case ascorbic acid (or the salt thereof) is added to the medium, its concentration is preferably 5 to 40 µg/mL, more preferably 10 to 30 µg/mL, and still more preferably about 20 µg/mL. In the case chondroitin sulfate (or the salt thereof) is added to the medium, its concentration is preferably 0.04 to 0.12% (w/v), more preferably 0.06 to 0.10%(w/v), and still more preferably about 0.08%(w/v). Further to the medium, antibiotics such as gentamicin, and pH indicators such as phenol red may be added as needed. And when the use of FCS, one of biological materials, is not desirable, serum free medium may be used.

In the present invention, as the medium for human corneal endothelial cell culture, a medium containing a Rho kinase inhibitor such as hexahydro-1-(isoquinolin-5-ylsulfonyl)-1H-1,4-diazepine (fasudil), 1-(5-Isoquinolinesulfonyl)homopiperazine (Y-27632), Glycyl-H-1152 dihydrochloride, 3-(4-Pyridyl) indole, N-(4-Pyridyl)-N'-(2,4,6-trichlorophenyl) urea or the salt thereof may be used. In the case that Y-27632 is added as Rho kinase inhibitor, its concentration is preferably 0.5 to 2.0 µmol/L, more preferably 1.0 to 1.8 µmol/L, and still more preferably about 1.5 µmol/L.

As the medium for human corneal endothelial cell culture, a medium supplemented with ALK-5 inhibitor such as SB431542, A-83-01, or the salt thereof may also be used. In the case that SB431542 is added as ALK-5 inhibitor, its concentration is preferably 0.5 to 1.5 µmol/L, more preferably 0.7 to 1.2 µmol/L, and still more preferably about 1 µmol/L. ALK-5 inhibitor may be used alone or together with other Rho kinase inhibitor.

In the present invention, human corneal endothelial cells used in the primary culture are the cells separated from a human corneal tissue. Human corneal tissue commercially available for research may be used as such a human corneal tissue, but the human corneal tissue donated to eye bank may also be used, provided that Declaration of Helsinki, national laws, and notifications of national regulatory authorities have been complied with.

In the present invention, the culture of human corneal endothelial cells is performed using a MSC conditioned medium, a medium containing MSC conditioned medium (or the concentrated solution thereof), or these media supplemented with one or more of other gradients selected from growth factor such as EGF, bFGF, NGF, IGF, and insulin, ascorbic acid, chondroitin sulfate, antibiotics, Rho kinase inhibitor, ALK-5 inhibitor, and so on, as a medium for human corneal endothelial cell culture. And the cell culture flask used in the culture of human corneal endothelial cells is preferably the flask whose bottom is preferably coated with collagen, fibronectin, and the like, or a flask whose bottom is modified by negatively charged functional group, such as CULTURE WARE FOR PRIMALIA (mfd. by BD).

In the present invention, the primary culture performed by seeding human corneal endothelial cells separated from human corneal tissue in the manner that the bottom of cell culture flask is occupied by the cells preferably to 20 to 50%, more preferably to 25 to 40%, still more preferably to about one third. In the primary culture, the human corneal endothelial cells are cultured until the bottom surface of the culture vessel is occupied by the cells preferably to 70% or more, and more preferably to a confluent state.

Human corneal endothelial cell may be subcultured following the primary culture. In the subculture, the human corneal endothelial cells are seeded in the manner that the cells occupied the bottom of cell culture flask to preferably 20 to 50%, more preferably 25 to 40%, still more preferably to about one third. The medium for human corneal endothelial cell culture used in the subculture may be the same medium used in the primary culture, but also the medium different from the primary medium may be used. In the primary culture, the human corneal endothelial cell is cultured until the bottom surface of the culture vessel is occupied by the cells preferably to 70% or more, and more preferably to a confluent state. Subculture may be repeated without particular limitation, provided that no change in cell morphology or the like appears under a microscope, but preferably repeated one to five times. During the primary culture and the following subculture, the number of the human corneal endothelial cells separated from the human corneal tissue multiplies by 200 times or more.

In the present invention, the term "human corneal endothelial cell" means not only the human corneal endothelial cell constituting human corneal endothelium but also the cell obtained by the primary culture or the subculture which composes single layer and shows polygonal shape on the inner surface of the cell culture flask when observed under a microscope.

It has known that human corneal endothelial cells, when cultured in vitro, produce fibroblast-like cells in general. In the present invention, the ratio of fibroblast-like cells in the cells obtained by the primary culture or the subculture (the number of fibroblast-like cell/total cell number×100%) is preferably less than 0.5%, more preferably less than 0.2%, and still more preferably less than 0.1% when observed under a microscope. The cells in which the ratio of the fibroblast-like cells is more than 1% cannot be used as the cells for transplantation. And the cell density on the inner surface of cell culture flask is preferably 1500 cell/mm$^2$ or more, and more preferably 1800 cell/mm$^2$ or more, when the cells reached confluence.

And the ratio of the cells which are positive for both of Na+/K+-ATPase and ZO-1 (double positive) in the cells obtained by the primary culture or the subculture (the number of double positive cell/total cell number×100%) is preferably 80% or more, more preferably 90% or more, and still more preferably 95% or more. The cells in which the ratio of the double positive cell is less than 50% cannot be used as the cells for transplantation.

In the present invention, the human corneal endothelial cells obtained by the primary culture or the subculture are detached from a cell culture flask by using a enzyme such as trypsin and collagenase, washed with PBS and the like to remove the enzyme, and suspended in a desired buffer solution at a desired concentration, and then this suspension may be used as the cells for transplantation to the patient suffering from corneal endothelial dysfunction such as bullous keratopathy. As the buffer solution used herein, acetated Ringer's solution and bicarbonated Ringer's solution may be preferably used. The transplantation of the cells to the patient may be carried out by injecting the cell suspension contained the desired number of the cells into a patient's eyeball using a syringe. The cells injected into the patient's eyeball are to be engrafted and show the function as corneal endothelial cells.

And the human corneal endothelial cells may be stored in a frozen state until their use. The cryopreservation of the human corneal endothelial cells is conducted in liquid nitrogen by suspending the cells in a cryopreservative agent and dispensing the suspension into tubes. As the cryopreservative agent, acetated Ringer's or bicarbonated Ringer's solution containing 20% DMSO and 8.8% albumin may be used. The cells thus stored in a frozen state may be commercially distributed as cell drugs and provided to medical institutions.

EXAMPLE 1

While the present invention will be described in further detail below referring to examples, it is not intended that the present invention be limited to the examples.

[Preparation of the Conditioned Medium of Human Mesenchymal Stem Cells (hMSC Conditioned Medium)]

The human mesenchymal stem cells derived from human bone marrow were seeded on 150 mm cell culture dish (mfd. by Corning) at the density of 5,000 to 10,000 cells/cm$^2$, and cultured to become subconfluent using 10% FCS/DMEM medium. After washed with PBS(−) twice, the cells were detached from the cell dish by trypsin treatment, and then added with 10% FCS/DMEM medium and suspended. The cells were collected by centrifugation (1200 rpm, 5 minutes). The cells thus collected were suspended with 10% FCS/DMEM medium and then seeded on 150 mm cell culture dish (mfd. by Corning) at the density of 3,000 to 5,000 cells/cm$^2$, and cultured until the cell density reached 50 to 70%. After the medium was discarded, added was 40 mL of Opti-MEM™ I Reduced-Serum Medium Liquid (mfd. by Gibco) medium supplemented with 8% FCS, 200 µg/mL of $CaCl_2 \cdot 2H_2O$, 0.08% (w/v) Chondroitin Sulfate C Sodium (WAKO), and 50 µg/mL of gentamicin, and the cells were cultured for about 16 hours. After the incubation, the medium was collected and centrifuged (1500 rpm, 5 minutes), and the supernatant thus obtained was filtrated through 0.2 µm membrane filter. And then 40 mL of new medium was added to the dish, and the cells were further cultured. Subsequently, the collection of the medium and the addition of the new medium were repeated every 12 to 24 hours for 3 to 5 days. The medium thus collected was centrifuged (1500 rpm, 5 minutes), and the supernatant thus obtained was filtrated through 0.2 µm membrane filter. The filtrated medium was designated a conditioned medium of human mesenchymal stem cell (hMSC conditioned medium). The hMSC conditioned medium was stored at 4° C. or at a frozen state (−30° C.), and when stored at 4° C., the storage life was limited to 10 days.

[Primary Culture of Human Corneal Endothelial Cell]

Human corneal endothelial cells were detached from a human corneal tissue for laboratory use (mfd. by Seattle Eye Bank) together with basement membrane (Descemet's membrane) using tweezers.

To the detached human corneal endothelial cells were added Opti-MEM™ I Reduced-Serum Medium supplemented with collagenase at a concentration of 1 mg/mL, and then the cells were allowed to stand to separate the human corneal endothelial cells from the basement membrane.

And then, the cells were lightly mixed to be suspended, and to the cells were added a basal medium for human corneal endothelial cell culture (an Opti-MEM™ I Reduced-Serum Medium Liquid supplemented with 8% FCS, 200 µg/mL of $CaCl_2\ 2H_2O$, 0.08%(w/v) chondroitin sulfate, 20 µg/mL of ascorbic acid, 50 µg/mL of gentamicin, 5 ng/mL of EGF, and 1 µmol/L of SB431542 (mfd. by TOCRIS)), hereinafter referred to as "basal medium". And the cells were collected by centrifugation (1200 rpm, 5 minutes).

The cells were suspended with the hMSC conditioned medium, and seeded on cell culture dish (mfd. by Corning)

in a condition that one third of the bottom of the flask was occupied by the cells. As a control culture, the cells were cultured using the basal medium in the same manner. Herein, the basal medium for human corneal endothelial cell culture (the basal medium) is a medium disclosed in a prior art (Joyce N C. et al., Cornea 23, S8-19 (2004)) with modification such as being free from NGF and pituitary extract. The primary culture was conducted until the cells reached confluence, and during this period, the medium was exchanged every 2 days.

[Subculture of Human Corneal Endothelial Cell]

The human corneal endothelial cells, the cells cultured in the primary culture as above until the cells reached confluence, were washed with PBS (−) twice, and then detached by trypsin treatment. The cells were suspended by the addition of the basal medium, and collected by centrifugation. The cells were suspended with the hMSC conditioned medium, seeded on a cell culture dish in a condition that one third of the bottom of the dish was occupied by the cells, and then cultured until confluent. As a control culture, the cells were cultured using the basal medium in the same manner.

[Morphological Evaluation of the Cells]

When the cells reached confluence in the primary culture of the human corneal endothelial cells as above, the cells were morphologically observed under a phase-contrast microscope at the time. As a result, there no fibroblast-like cell were observed in the cells cultured with the hMSC conditioned medium, and almost all the cells were single layered and polygonally-shaped cells similar to normal human corneal endothelial cells. And the ratio of fibroblast-like cell was estimated less than 1/500, because all the cells observed under a microscope (about 500 cells) showed polygonally-shape (FIG. 1-A). On the other hand, 50% or more of the cells showed the morphology of spindle-shaped fibroblast-like cell in the control culture (FIG. 1-B). The fibroblast-like cell was considered to cause the corneal opacification, when transplanted as a human corneal endothelial cell. Therefore it is required that the cells to be transplanted as human corneal endothelial cells are free from such fibroblast-like cells. The cells obtained by culture using the hMSC conditioned medium suffice this requirement.

And when the cells reached confluence, the cell density on the cell culture dish was measured using a software for measuring density of corneal endothelial cell (Konan Medical Inc. KSS-400EB software). The cell density of the control-cultured cells was measured to be 1202 cell/mm$^2$, but the density of the cells cultured with hMSC conditioned medium was measured to be 1845 cell/mm$^2$.

Considering that the cell density of corneal endothelium decreases in the patient with corneal dysfunction, the cells cultured using hMSC conditioned medium, which are capable to grow to a high cell density, are expected to be highly effective as the cells for use in transplantation to the patient.

[Measurement of Expression Levels of TGF Related Genes by Real-Time PCR Method]

240 days after the beginning of the primary culture (the subculture was conducted 7 times), total mRNA was extracted from the corneal endothelial cells using RNeasy (mfd. by QIAGEN), and then using the total mRNA thus extracted as the template, the reverse transcription reaction (42° C., 60 minutes) was conducted by the oligo dT method using ReverTra Ace (mfd. by TOYOBO) to synthesize the single strand DNA. Using this single strand DNA as template, the expression levels of TGFβ1, TGFβ2, TGFβ type I receptor (TGFβR1), and TGFβ type II receptor (TGFβR2) genes, were compared between the cells cultured in the basal medium and in the hMSC conditioned medium, respectively, by the real-time PCR method using TaqMan™ Fast Advanced Master Mix (mfd. by Applied Biosystems). In doing this, GAPDH gene was used as the internal standard of the real-time PCR method. And PCR reaction was performed for 40 cycles (95° C. for 15 seconds and 60° C. for 30 seconds) using StepOne™ real-time PCR system (mfd. by Applied Biosystems) The PCR reaction was conducted by using TaqMan™ primers (mfd. by Invitrogen) as below: Hs99999918_m1 for TGFβ1; Hs00234244_m1 for TGFβ2; Hs00610320_m1 for TGFβR1; Hs00234253_m1 for TGFβR2; and Hs00266705_g1 for GAPDH.

The expression levels of all of TGFβ1, TGFβ2, TGFβR1, and TGFβR2 genes in the cells cultured in the hMSC conditioned medium were less than those in the cells cultured in the basal medium (control culture) (FIG. 2). TGFβ1 and TGFβ2 are known to induce the differentiation of corneal endothelial cells via their receptors. The differentiation induction via TGF therefore was considered to be suppressed more in the cells cultured in the hMSC conditioned medium than in the control-cultured cells, and the cells cultured in the hMSC conditioned medium are considered to be more similar to stem cells in the characters.

[Measurement of Expression Levels of Fibroblast Related Genes by Real-Time PCR Method]

And then the expression levels of collagen type I, fibronectin, and collagen type IV genes were compared between the cells cultured in the basal medium and the hMSC conditioned medium, respectively, by the real-time PCR method. In doing this, GAPDH gene was used as the internal standard of the real-time PCR method. The PCR reaction was conducted by using TaqMan™ primers (mfd. by Invitrogen) as below: Hs00164004_m1 for collagen type I; Hs01549976_m1 for fibronectin; Hs00266237_m1 for collagen type IV; and Hs00266705_g1 for GAPDH were used.

The expression levels of collagen type I and fibronectin genes in the cells cultured in the hMSC conditioned medium were markedly lower than those in the cells cultured in the basal medium (control culture) (FIG. 3-A, B). Both Collagen type I and fibronectin are known to strongly express in fibroblasts, but weakly express in normal human corneal endothelial cells. As shown in FIG. 1-A, almost all the cells cultured in the hMSC conditioned medium were single layered and polygonally-shaped cells morphologically similar to normal human corneal endothelial cells, and no fibroblast was observed. The marked reduction of the expression levels of these genes indicates that fibroblast-like cells rarely develop when culturing human corneal endothelial cells in the hMSC conditioned medium on a genetic level. No difference was observed in the expression level of collagen type IV between both of the cells (FIG. 3-C).

[Measurement of the Expression Level of Functional Markers of Corneal Endothelial Cell]

210 days after the beginning of the primary culture (the subculture was conducted 4 times), each of the human corneal endothelial cells cultured in the control culture and in the hMSC conditioned medium was detached from the culture flask by trypsin treatment, and the detached cells were collected by centrifugation. And then each of the cells was suspended with the basal medium and the hMSC conditioned medium, respectively, and then seeded on a 48 well plate (mfd. by Corning) at a density of 300 cell/mm$^2$ and cultured overnight. The medium was exchanged to the new same medium, and the cells were further cultured for 6 days. After culture, the cells were fixed by submerged in 4% paraformaldehyde for 10 minutes at room temperature and permeabilized by acid-alcohol solution. The cells subsequently were allowed to stand in blocking solution (PBS containing 10% fetal calf serum) for 1 hour at room temperature, and after adding anti-human Na+/K+-ATPase antibody or anti-human ZO-1 antibody, let stand for 1 hour at room temperature. After removing the antibody solutions and washing the cells with PBS (−) thrice, ALEXA488 Antibody (mfd. by Molecular Probes) or ALEXA594 goat anti-mouse IgG antibody (mfd. by Molecular Probes) was added and the cells were allowed to stand for 1 hour at room temperature. After removing the antibody solutions and washing the cells with PBS (−) thrice, the cells were photographed by fluorescence microscope (TCS SP2 AOBS, mfd. by Leica Microsystems). The results showed that almost all the cells (at least not less than 80%) were positive for both Na+/K+-ATPase positive and ZO-1.

Na+/K+-ATPase is one of the proteins having a pump function to modulate the amount of water in cornea, one of the function of corneal endothelial cells. ZO-1 is one of the proteins composing tight junction of corneal endothelial cells and is involved in the barrier function of corneal endothelial cell. As the cells obtained by culturing in the hMSC conditioned medium were positive for both of Na+/K+-ATPase and ZO-1, the cells are considered to possess both of the pump function and the barrier function which are the primary function of the endothelial cells, and therefore the functional improvement of corneal endothelium is expected by transplanting the cells to the patient with corneal dysfunction

[Measurement of Cell Growth by BrdU Uptake Rate]

240 days after the beginning of the primary culture (the subculture was conducted 5 times), each of the human corneal endothelial cells cultured in the control culture and in the hMSC conditioned medium was detached from the culture flask by trypsin treatment, and the detached cells were collected by centrifugation. Each of the cells was suspended with the basal medium and the hMSC conditioned medium, respectively, and then seeded on a 96 well plate at a density of 5,000 cell/mm$^2$ and cultured overnight. The medium was exchanged to the new same medium, and the cells were further cultured for 5 days. And 5-bromo-2'-deoxyuridine (BrdU) was added to the medium, the cells were cultured overnight. Then the medium was discarded, and after adding a fixing solution (Amersham cell proliferation biotrak ELISA system, ver2, mfd. by GE), the cells were incubated for 30 minutes at room temperature. And then, the fixing solution was discarded, and after adding a blocking solution (Amersham cell proliferation biotrak ELISA system, ver2, mfd. by GE), the cells were allowed to stand for 30 minutes at room temperature. And then, the blocking solution was discarded, and after adding a peroxidase-conjugated anti-BrDU antibody, the cells were allowed to stand for 2 hours at room temperature. The cells were washed with washing buffer thrice, and after adding with TMB (3,3',5,5'-tetramethylbenzidine) substrate (Amersham cell proliferation biotrak ELISA system, ver2, mfd. by GE), the cells were allowed to stand for 5 to 30 minutes. 1M sulfuric acid was added to terminate the reaction, and absorbance at the wave length of 450 nm was measured by a plate leader. The result was shown as the mean±SEM of 5 determinations.

The results showed that BrdU uptake rate of the cells cultured in hMSC conditioned medium was about one and half as high as that of the cells cultured in basal medium, which indicates that the cells cultured in hMSC conditioned medium actively proliferated (FIG. 4).

[Measurement of the Expression Level of Ki-67 Protein]

240 days after the beginning of the primary culture (the subculture was conducted 5 times), each of the human corneal endothelial cells cultured in the control culture and in the hMSC conditioned medium was detached from the culture flask by trypsin treatment, and the detached cells were collected by centrifugation. Each of the cells was suspended with the basal medium and the hMSC conditioned medium, respectively, and then seeded on a 96 well plate at a density of 5,000 cell/mm$^2$ and cultured overnight. The medium was exchanged to the new same medium, and the cells were further cultured for 5 days. After culture, the cells were fixed by submerged in 4% paraformaldehyde for 10 minutes at room temperature and permeabilized by acid-alcohol solution. Then, the cells were allowed to stand in blocking solution (PBS containing 10% fetal calf serum) for 1 hour at room temperature, and after adding anti-human Ki-67 antibody (mfd. by DAKO), the cells were allowed to stand for 1 hour at room temperature. After removing the antibody solutions and washing the cells with PBS (−) thrice, ALEXA488 antibody (mfd. by Molecular Probe) was added and the cells were allowed to stand for 1 hour at room temperature. After removing the antibody solution and washing the cells with PBS (−) thrice, the cells were submerged in Vector Shield (mfd. by Vector Laboratories) containing DAPI nuclear stain to stain the Ki-67 positive cells. The stained cells were photographed by fluorescence microscope (BZ—9000, mfd. by KEYENCE), and the ratio of the Ki-67 positive cell was calculated by observing about 300 cells.

As a result, the ratio of Ki-67 positive cell in the cells cultured with hMSC conditioned medium was calculated as 15.8%, which was significantly higher than that in the cells cultured in the basal medium (10.8%), (FIG. 5). Ki-67 protein has known to be a nuclear protein promoting cell growth. These results therefore show the active proliferation of the cells cultured with hMSC conditioned medium on a genetic level.

Combined with the results of the measurements of the expression level of the TGF related genes by real-time PCR method and the BrdU uptake rate as shown above, the cells cultured with hMSC conditioned medium were considered to possess more stem-cell like properties and more actively grow than the cells of control culture. Therefore, when transplanted to the patient with corneal endothelial dysfunction accompanied by the decrease of corneal endothelial cell density, the cells obtained by culturing with the hMSC conditioned medium are expected to maintain their properties for a comparatively prolonged time in the transplanted tissue, to maintain at a high level the corneal endothelial cell density, the most important clinical parameter of the corneal endothelium, and to improve the function of corneal endothelium.

[Addition Test of Concentrated Solution of hMSC Conditioned Medium]

Human corneal endothelial cells were mechanically detached from a human corneal tissue for laboratory use (mfd. by Seattle Eye Bank) with basement membrane (Descemet's membrane). After adding collagenase solution, the detached human corneal endothelial cells were allowed to stand to separate the cells from the basement membrane. And then, the cells were lightly mixed to be suspended, and after adding a basal medium for human corneal endothelial cell culture (an Opti-MEM™ I Reduced-Serum Medium Liquid supplemented with 8% FCS, 200 µg/mL of $CaCl_2 \cdot 2H_2O$, 0.08%(w/v) chondroitin sulfate, 20 µg/mL of ascorbic acid, 50 µg/mL of gentamicin, 5 ng/mL of EGF, and 1

μmol/L of SB431542 (mfd. by TOCRIS)), and the cells were collected by centrifugation (1200 rpm, 5 minutes).

The cells were seeded on a cell culture dish in the manner that the cells occupied the bottom of the cell culture dish to one third, and were cultured in the basal medium supplemented with the concentrated solution of hMSC conditioned medium which was prepared by the method described below. The concentrated solution of hMSC conditioned medium was added in the ration of 1% (v/v), 3% (v/v), or 10% (v/v) to the basal medium.

The cell growth was measured by BrdU uptake rate as above. The results showed that BrdU uptake rate of the cells increased depending on the concentration of the concentrated solution of hMSC conditioned medium added supplementary, which suggests the concentrated solution of hMSC conditioned medium exerts the effect to promote the growth of the human corneal endothelial cells (FIG. 6). The cells cultured in the medium supplemented with 10% (v/v) of the concentrated solution of hMSC conditioned medium showed almost identical BrdU uptake rate to that of the cells cultured in hMSC conditioned medium (FIG. 6).

[Preparation of Concentrated Solution of Conditioned Medium of Human Mesenchymal Stem Cell (Concentrated Solution of hMSC Conditioned Medium)]

$2 \times 10^6$ cells of the human mesenchymal stem cells were seeded on a 150 mm cell culture dish, and cultured overnight with an Opti-MEM™ I Reduced-Serum Medium Liquid supplemented with 8% FCS, 200 μg/mL of $CaCl_2$-$2H_2O$, 0.08%(w/v) chondroitin sulfate, and 50 μg/mL of gentamicin. The medium was exchanged to non-serum medium (Opti-MEM™ I Reduced-Serum Medium Liquid supplemented with 200 μg/mL of $CaCl_2.2H_2O$, 0.08%(w/v) chondroitin sulfate, 50 μg/mL of gentamicin), and the cells were cultured for 48 hours. After culture, the culture solution was collected by centrifugation (1500 rpm, 5 minutes). The supernatant thus collected was concentrated to about 17 times by using an ultrafiltration unit (3 kDa cut off, Amicon Ultra-PL 3, mfd. by Millipore), what obtained was referred to as the concentrated solution of hMSC conditioned medium.

[Large Scale Production of Human Corneal Endothelial Cells by Subculture]

The human corneal endothelial cells were cultured to be confluent in the primary culture described above. The human corneal endothelial cells were washed with PBS (–) twice, and then detached by trypsin treatment. The cells were suspended by the addition of the basal medium, and collected by centrifugation. The cells were suspended with the hMSC conditioned medium, seeded on the cell culture dish in a condition that one third of the bottom of the dish was occupied by the cells, and then cultured until confluent. This subculture was repeated 5 times. As a result, it was confirmed that the cells cultured with hMSC conditioned medium can be subcultured at least 5 times, and that the cell number can be multiplied at least 270-fold by the subculture. That is, the method for culture of the human corneal endothelial cell using the hMSC conditioned medium was considered to be a effective way to produce the corneal endothelial cells for transplantation in large amount. By using the method for culture as such, enough amount of the corneal endothelial cell for transplantation can be provided to medical institutions, and the donor shortage is expected to be resolved in the therapy of the patient with corneal endothelial dysfunction.

INDUSTRIAL APPLICABILITY

The present invention enables to stably provide the corneal endothelial cells which have a constant quality and can be transplanted to a patient with corneal endothelial dysfunction.

The invention claimed is:

1. A method for culturing human corneal endothelial cells, which comprises
    a step for preparing a conditioned medium by culturing a mesenchymal stem cell in a medium containing chondroitin sulfate,
    a step for separating the human corneal endothelial cells from a corneal tissue, and
    a step for propagating the separated human corneal endothelial cells by a culture using a medium for corneal endothelial cell culture consisting of the conditioned medium of mesenchymal stem cells or containing the conditioned medium wherein the mesenchymal stem cell is a human mesenchymal stem cell and wherein the concentration of chondroitin sulfate is 0.04 to 0.12 % (w/v).

2. The method according to claim 1, wherein the medium for corneal endothelial cell culture contains the conditioned medium in a proportion of 0.5 to 50 % (v/v).

3. The method according to claim 1, wherein the medium for corneal endothelial cell culture contains the conditioned medium in a proportion of 1to 10 % (v/v).

4. The method according to claim 1, wherein the concentration of chondroitin sulfate is 0.08 % (w/v).

5. The method according to claim 1, wherein the mesenchymal stem cell is a mesenchymal stem cell derived from human bone marrow.

6. A method for culturing human corneal endothelial cells, which comprises
    a step for preparing a conditioned medium by culturing a mesenchymal stem cell in a medium containing chondroitin sulfate,
    a step for preparing a concentrated solution by filtration concentration of the conditioned medium,
    a step for separating the human corneal endothelial cells from a corneal tissue, and
    a step for propagating the separated human corneal endothelial cells by a culture using a medium for corneal endothelial cell culture containing the concentrated solution wherein the mesenchymal stem cell is a human mesenchymal stem cell and wherein the concentration of chondroitin sulfate is 0.04 to 0.12 % (w/v).

7. The method according to claim 6, wherein the concentration rate in the filtration concentration is 2 to 30 times.

8. The method according to claim 6, wherein the concentration rate in the filtration concentration is 15 to 20 times.

9. The method according to claim 6, wherein the medium for corneal endothelial cell culture contains the concentrated solution at a proportion of 0.5 to 50 % (v/v).

10. The method according to claim 6, wherein the medium for corneal endothelial cell culture contains the concentrated solution at a proportion of 1 to 10 % (v/v).

11. The method according to claim 6, wherein the concentration of chondroitin sulfate is 0.08 % (w/v).

12. The method according to claim 6, wherein the mesenchymal stem cell is a mesenchymal stem cell derived from human bone marrow.

13. The method according to claim 1, wherein the medium for corneal endothelial cell culture is not added with nerve growth factor.

14. The method according to claim 6, wherein the medium for corneal endothelial cell culture is not added with nerve growth factor.

* * * * *